United States Patent [19]
Bergsma et al.

[11] Patent Number: 6,020,157
[45] Date of Patent: Feb. 1, 2000

[54] POLYNUCLEOTIDES ENCODING HFGAN72X RECEPTOR

[75] Inventors: Derk J. Bergsma, Berwyn, Pa.; Catherine Elizabeth Ellis, Glassboro, N.J.

[73] Assignee: SmithKline Beecham Corporation, Philadelphia, Pa.

[21] Appl. No.: 08/846,704

[22] Filed: Apr. 30, 1997

[51] Int. Cl.[7] ............................ C12N 15/09; C07K 14/705
[52] U.S. Cl. ................ 435/69.1; 435/252.3; 435/254.11; 435/320.1; 435/325; 536/23.5
[58] Field of Search ................................ 435/69.1, 320.1, 435/252.3, 254.11, 325; 536/23.5

[56] References Cited

FOREIGN PATENT DOCUMENTS

| | | |
|---|---|---|
| 8-266280 | 10/1996 | Japan . |
| WO96/05302 | 2/1996 | WIPO . |
| WO 96/34877 | 11/1996 | WIPO . |

OTHER PUBLICATIONS

George et al., Macromolecular Sequencing & Synthesis, 127–149, 1988.

*Primary Examiner*—Sally P. Teng
*Attorney, Agent, or Firm*—Elizabeth J. Hecht; William T. Han; William T. King

[57] ABSTRACT

HFGAN72X polypeptides and polynucleotides and methods for producing such polypeptides by recombinant techniques are disclosed. Also disclosed are methods for utilizing HFGAN72X polypeptides and polynucleotides in the design of protocols for the treatment of infections such as bacterial, fungal, protozoan and viral infections, particularly infections caused by HIV-1 or HIV-2; pain; cancers; anorexia; bulimia; asthema; Parkinson's disease; acute heart failure; hypotension; hypertension; unary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others and diagnostic assays for such conditions.

11 Claims, No Drawings

POLYNUCLEOTIDES ENCODING HFGAN72X RECEPTOR

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to G-protein coupled receptor family, hereinafter referred to as HFGAN72X. The invention also relates to inhibiting or activating the action of such polynucleotides and polypeptides.

BACKGROUND OF THE INVENTION

It is well established that many medically significant biological processes are mediated by proteins participating in signal transduction pathways that involve G-proteins and/or second messengers, e.g., cAMP (Lefkowitz, Nature, 1991, 351:353–354). Herein, these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K, et al., Science, 1987, 238:650–656; Bunzow, J. R, et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is the activation of the enzyme, adenylate cyclase, inside the cell. Enzyme activation by hormones is dependent on the presence of the nucleotide GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 transmembrane (7TM) receptors have been successfully introduced onto the market.

This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulmia; asthma; Parkinson's disease; acute heart failure; hypotension; hypertension; urinary retention; osteoporosis; angina pectoris; myocardial infarction; ulcers; asthma; allergies; benign prostatic hypertrophy, and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to HFGAN72X polypeptides and recombinant materials and methods for their production. Another aspect of the invention relates to methods for using such HFGAN72X polypeptides and polynucleotides. Such uses include the treatment of infections such as bacterial fungal protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with HFGAN72X imbalance with the identified compounds. Yet another aspect of the invention relates to diagnostic assays for detecting diseases associated with inappropriate HFGAN72X activity or levels.

DESCRIPTION OF THE INVENTION

Definitions

The following definitions are provided to facilitate understanding of certain terms used frequently herein.

"HFGAN72X" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said HFGAN72X including similar activities or improved activities or these activities with decreased undesirable side-effects. Also included are antigenic and immunogenic activities of said HFGAN72X.

"HFGAN72X gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", Ann NY Acad Sci (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code.

A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to HFGAN72X polypeptides. The HFGAN72X polypeptides include the polypeptide of SEQ ID NO: 2 and the known polypeptide of SEQ ID NO: 4; as well as polypeptides comprising the amino acid sequence of SEQ ID NO: 2; and polypeptides comprising the amino acid sequence which have at least 80% identity to that of SEQ ID NO: 2 over its entire length, and still more preferably at least 90% identity, and even still more preferably at least 95% identity to SEQ ID NO: 2. Furthermore, those with at least 97–99% are highly preferred. Also included within HFGAN72X polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably HFGAN72X polypeptides exhibit at least one biological activity of the receptor.

The HFGAN72X polypeptides may be in the form of the "mature" protein or may be a part of a larger protein such as a fusion protein. It is often advantageous to include an additional amino acid sequence which contains secretory or leader sequences, prosequences, sequences which aid in purification such as multiple histidine residues, or an additional sequence for stability during recombinant production.

Fragments of the HFGAN72X polypeptides are also included in the invention. A fragment is a polypeptide having an amino acid sequence that entirely is the same as part, but not all, of the amino acid sequence of the aforementioned HFGAN72X polypeptides. As with HFGAN72X polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HFGAN72X polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HFGAN72X polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is the known polypeptide having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HFGAN72X polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HFGAN72X polynucleotides. HFGAN72X polynucleotides include isolated polynucleotides which encode the HFGAN72X polypeptides and fragments, and polynucleotides closely related thereto. More specifically, HFGAN72X polynucleotide of the invention include a polynucleotide comprising the nucleotide sequence set forth in SEQ ID NO: 1 encoding a HFGAN72X polypeptide of SEQ ID NO: 2, and a polynucleotide having the particular sequence of SEQ ID NO: 1 and the known sequence of SEQ ID NO:3. HFGAN72X polynucleotides further include a polynucleotide comprising a nucleotide sequence that has at least 80% identity to a nucleotide sequence encoding the HFGAN72X polypeptide of SEQ ID NO:2 over its entire length, and a polynucleotide that is at least 80% identical to that having SEQ ID NO: 1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under HFGAN72X polynucleotides are a nucleotide sequence which has sufficient identity to a nucleotide sequence contained in SEQ ID NO: 1 to hybridize under conditions useable for amplification or for use as a probe or marker. The invention also provides polynucleotides which are complementary to such HFGAN72X polynucleotides.

HFGAN72X of the invention is structurally related to other proteins of the G-protein coupled receptor family, as shown by the results of sequencing the cDNA encoding human HFGAN72X. The cDNA sequence of SEQ ID NO: I contains an open reading frame (nucleotide numbers 154 to 1428) encoding a polypeptide of 425 amino acids of SEQ ID NO:2. The amino acid sequence of Table 1 (SEQ ID NO:2) has about 30% identity (using FASTA, Non-redundant Protein Data Base) in 209 amino acid residues with Neurokinin-1 Receptor, (Biochem. Biophys. Res. Commun. 180(2) 1110–1117, 1991). Furthermore, HFGAN72X (SEQ ID NO:2) is 29% identical to Human Neurokinin-3 Receptor over 248 amino acids residues (FEBS Lett. 299(1) 90–95, 1992). The nucleotide sequence of Table 1 (SEQ ID NO:1) has about 53% identity (using FASTA) in 618 nucleotide residues with Rat Substance P/Neurokinin-1 Receptor (J. Biol. Chem. 264, 17649–17652, 1989). Furthermore, HFGAN72X (SEQ ID NO: 1) is 57% identical to Human Somatostatin Type 5 Receptor polynucleotide over 426 nucleotide residues (Mol. Pharmacol. 45(3) 417–427, 1994).

TABLE 1[a]

| | | | | |
|---|---|---|---|---|
| 1 | CCTCCCTTCA | GGAAGTTTGA | GGCTGAGACC | CGAAAAGACC | TGGGTGCAAG |
| 51 | CCTCCAGGCA | CCCTGAAGGG | AGTGGACTGA | GGGCTGGCCC | AAGCTCCCTC |
| 101 | CTCTCCCTCT | GTAGAGACTA | GGATGCCCCT | CTGCTGCAGC | GGCTCCTGAG |
| 151 | CTCATGGAGC | CCTCAGCCAC | CCCAGGGGCC | CAGATGGGGG | TCCCCCCTGG |
| 201 | CAGCAGAGAG | CCGTCCCCTG | TGCCTCCAGA | CTATGAAGAT | GAGTTTCTCC |
| 251 | GCTATCTGTG | GCGTGATTAT | CTGTACCCAA | AACAGTATGA | GTGGGTCCTC |
| 301 | ATCGCAGCCT | ATGTGGCTGT | GTTCGTCGTG | GCCCTGGTGG | GCAACACGCT |
| 351 | GGTCTGCCTG | GCCGTGTGGC | GGAACCACCA | CATGAGGACA | GTCACCAACT |
| 401 | ACTTCATTGT | CAACCTGTCC | CTGGCTGACG | TTCTGGTGAC | TGCTATCTGC |
| 451 | CTGCCGGCCA | GCCTGCTGGT | GGACATCACT | GAGTCCTGGC | TGTTCGGCCA |
| 501 | TGCCCTCTGC | AAGGTCATCC | CCTATCTACA | GGCTGTGTCC | GTGTCAGTGG |
| 551 | CAGTGCTAAC | TCTCAGCTTC | ATCGCCCTGG | ACCGCTGGTA | TGCCATCTGC |
| 601 | CACCCACTAT | TGTTCAAGAG | CACAGCCCGG | CGGGCCCGTG | GCTCCATCCT |
| 651 | GGGCATCTGG | GCTGTGTCGC | TGGCCATCAT | GGTGCCCCAG | GCTGCAGTCA |

TABLE 1ᵃ-continued

```
 701   TGGAATGCAG CAGTGTGCTG CCTGAGCTAG CCAACCGCAC ACGGCTCTTC

751   TCAGTCTGTG ATGAACGCTG GGCAGATGAC CTCTATCCCA AGATCTACCA

801   CAGTTGCTTC TTTATTGTCA CCTACCTGGC CCCACTGGGC CTCATGGCCA

851   TGGCCTATTT CCAGATATTC CGCAAGCTCT GGGGCCGCCA GATCCCCGGC

901   ACCACCTCAG CACTGGTGCG GAACTGGAAG CGCCCCTCAG ACCAGCTGGG

951   GGACCTGGAG CAGGGCCTGA GTGGAGAGCC CCAGCCCCGG GGCCGCGCCT

1001   TCCTGGCTGA AGTGAAGCAG ATGCGTGCAC GGAGGAAGAC AGCCAAGATG

1051   CTGATGGTGG TGCTGCTGGT CTTCGCCCTC TGCTACCTGC CCATCAGCGT

1101   CCTCAATGTC CTTAAGAGGG TGTTCGGGAT GTTCCGCCAA GCCAGTGACC

1151   GCGAAGCTGT CTACGCCTGC TTCACCTTCT CCCACTGGCT GGTGTACGCC

1201   AACAGCGCTG CCAACCCCAT CATCTACAAC TTCCTCAGTG GCAAATTCCG

1251   GGAGCAGTTT AAGGCTGCCT TCTCCTGCTG CCTGCCTGGC CTGGGTCCCT

1301   GCGGCTCTCT GAAGGCCCCT AGTCCCCGCT CCTCTGCCAG CCACAAGTCC

1351   TTGTCCTTGC AGAGCCGATG CTCCATCTCC AAAATCTCTG AGCATGTGGT

1401   GCTCACCAGC GTCACCACAG TGCTGCCCTG AGCGAGGGCT GCCCTGGAGG

1451   CTCCGGcTCG GGGGATCTGC CCCTACCCCT CATGGaAAGA CAGCTGGATG

1501   TGGTGAAAGG CTGTGGATTC AGtCCTGGGT TTCTGCCTGT GTGACTCTGG

1551   ATAAGTCAcT TCCT
```

ᵃA nucleotide sequence of a human HFGAN72X. SEQ ID NO: 1.

TABLE 2ᵇ

```
  1    MEPSATPGAQ MGVPPGSREP SPVPPDYEDE FLRYLWRDYL YPKQYEWVLI

51    AAYVAVFVVA LVGNTLVCLA VWRNHHMRTV TNYFIVNLSL ADVLVTAICL

101    PASLLVDITE SWLFGHALCK VIPYLQAVSV SVAVLTLSFI ALDRWYAICH

151    PLLFKSTARR ARGSILGIWA VSLAIMVPQA AVMECSSVLP ELANRTRLFS

201    VCDERWADDL YPKIYHSCFF IVTYLAPLGL MAMAYFQIFR KLWGRQIPGT

251    TSALVRNWKR PSDQLGDLEQ GLSGEPQPRG RAFLAEVKQM RARRKTAKML

301    MVVLLVFALC YLPISVLNVL KRVFGMFRQA SDREAVYACF TFSHWLVYAN

351    SAANPIIYNF LSGKFREQFK AAFSCCLPGL GPCGSLKAPS PRSSASHKSL

401    SLQSRCSISK ISEHVVLTSV TTVLP
```

ᵇAn amino acid sequence of a human HFGAN72X. SEQ ID NO: 2.

One polynucleotide of the present invention encoding HFGAN72X may be obtained using standard cloning and screening, from a cDNA library derived from mRNA in cells of human Fetal Brain, Adult Brain, Placenta using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding the HFGAN72X polypeptide of SEQ ID NO:2 may be identical to the polypeptide encoding sequence contained in Table 1 (nucleotide numbers 154 to 1428 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of HFGAN72X polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro-protein sequence, or other fusion peptide portions.

For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding HFGAN72X variants comprising the amino acid sequence of the HFGAN72X polypeptide of Table 1 (SEQ ID NO:2) in which several, 5–10, 1–5, 1–3, 1–2 or 1 amino acid residues are substituted, deleted or added, in any combination. The sequence used as a probe to identify the HFGAN72X of the present invention is contained in Table 3 (SEQ ID NO: 3) encoding the amino acid sequence of Table 4 (SEQ ID NO: 4).

TABLE 3[c]

| | |
|---|---|
| 1 | CCTCCCTTCA GGAAGTTTGA GGCTGAGACC CGAAAAGACC TGGGTGCAAG |
| 51 | CCTCCAGGCA CCCTGAAGGG AGTGGACTGA GGGCTGGCCC AAGCTCCCTC |
| 101 | CTCTCCCTCT GTAGAGACTA GGATGCCCCT CTGCTGCAGC GGCTCCTGAG |
| 151 | CTCATGGAGC CCTCAGCCAC CCCAGGGGCC CAGATGGGGG TCCCCCCTGG |
| 201 | CAGCAGAGAG CCGTCCCCTG TGCCTCCAGA CTATGAAGAT GAGTTTCTCC |
| 251 | GCTATCTGTG GCGTGATTAT CTGTACCCAA AACAGTATGA GTGGGTCCTC |
| 301 | ATCGCAGCCT ATGTGGCTGT GTTCGTCGTG GCCCTGGTGG GCAACACGCT |
| 351 | GGTCTGCCTG GCCGTGTGGC GGAACCACCA CATGAGGACA GTCACCAACT |
| 401 | ACTTCATTGT CAACCTGTCC CTGGCTGACG TTCTGGTGAC TGCTATCTGC |
| 451 | CTGCCGGCCA GCCTGCTGGT GGACATCACT GAGTCCTGGC TGTTCGGCCA |
| 501 | TGCCCTCTGC AAGGTCATCC CCTATCTACA GGCTGTGTCC GTGTCAGTGG |
| 551 | CAGTGCTAAC TGTCAGCTTC ATCGCCCTGG ACCGCTGGTA TGCCATCTGC |
| 601 | CACCCACTAT TGTTCAAGAG CACAGCCCGG CGGGCCCGTG GCTCCATCCT |
| 651 | GGGCATCTGG GCTGTGTCGC TGGCCATCAT GGTGCCCCAG GCTGCAGTCA |
| 701 | TGGAATGCAG CAGTGTGCTG CCTGAGCTAG CCAACCGCAC ACGGCTCTTC |
| 751 | TCAGTCTGTG ATGAACGCTG GGCAGATGAC CTCTATCCCA AGATCTACCA |
| 801 | CAGTTGCTTC TTTATTGTCA CCTACCTGGC CCCACTGGGC CTCATGGCCA |
| 851 | TGGCCTATTT CCAGATATTC CGCAAGCTCT GGGGCCGCCA GATCCCCGGC |
| 901 | ACCACCTCAG CACTGGTGCG GAACTGGAAG CGCCCCTCAG ACCAGCTGGG |
| 951 | GGACCTGGAG CAGGGCCTGA GTGGAGAGCC CCAGCCCCGG GGCCGCGCCT |
| 1001 | TCCTGGCTGA AGTGAAGCAG ATGCGTGCAC GGAGGAAGAC AGCCAAGATG |
| 1051 | CTGATGGTGG TGCTGCTGGT CTTCGCCCTC TGCTACCTGC CCATCAGCGT |
| 1101 | CCTCAATGTC CTTAAGAGGG TGTTCGGGAT GTTCCGCCAA GCCAGTGACC |
| 1151 | GCGAAGCTGT CTACGCCTGC TTCACCTTCT CCCACTGGCT GGTGTACGCC |
| 1201 | AACAGCGCTG CCAACCCCAT CATCTACAAC TTCCTCAGTG GCAAATTCCG |
| 1251 | GGAGCAGTTT AAGGCTGCCT TCTCCTGCTG CCTGCCTGGC CTGGGTCCCT |
| 1301 | GCGGCTCTCT GAAGGCCCCT AGTCCCCGCT CCTCTGCCAG CCACAAGTCC |
| 1351 | TTGTCCTTGT AGAGCCGATG CTCCGTCTCC AAAATCTCTG AGCATGTGGT |
| 1401 | GCTCACCAGC GTCACCACAG TGCTGCCCTG AGCGAGGGCT GCCCTGGAGG |
| 1451 | CTCCGGNTCG GGGGATCTGC CCCTACCCCT CATGGNAAGA CAGCTGGATG |
| 1501 | TGGTGAAAGG CTGTGGATTC AGNCCTGGGT TTCTGCCTGT GTGACTCTGG |
| 1551 | ATAAGTCANT TCCT |

[c]A known partial nucleotide sequence of a human HFGAN72X. SEQ ID NO: 3.

TABLE 4[d]

| | | | | | |
|---|---|---|---|---|---|
| 1 | MEPSATPGAQ | MGVPPGSREP | SPVPPDYEDE | FLRYLWRDYL | YPKQYEWVLI |
| 51 | AAYVAVFVVA | LVGNTLVCLA | VWRNHHMRTV | TNYFIVNLSL | ADVLVTAICL |
| 101 | PASLLVDITE | SWLFGHALCK | VIPYLQAVSV | SVAVLTLSFI | ALDRWYAICH |
| 151 | PLLFKSTARR | ARGSILGIWA | VSLAIMVPQA | AVMECSSVLP | ELANRTRLFS |
| 201 | VCDERWADDL | YPKIYHSCFF | IVTYLAPLGL | MAMAYFQIFR | KLWGRQIPGT |
| 251 | TSALVRNWKR | PSDQLGDLEQ | GLSGEPQPRA | RAFLAEVKQM | RARRKTAKML |
| 301 | MVVLLVFALC | YLPISVLNVL | KRVFGMFRQA | SDREAVYACF | TFSHWLVYAN |
| 351 | SAANPIIYNF | LSGKFREQFK | AAFSCCLPGL | GPCGSLKAPS | PRSSASHKSL |
| 401 | SL | | | | |

[d] A known partial amino acid sequence of a human HFGAN72X. SEQ ID NO: 4.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO: 1 or a fragment thereof may be used as hybridization probes for cDNA and genomic DNA, to isolate full-length cDNAs and genomic clones encoding HFGAN72X and to isolate cDNA and genomic clones of other genes that have a high sequence similarity to the HFGAN72X gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding the HFGAN72X polypeptide comprises the steps of screening an appropriate library under stringent hybridization conditions with a labeled probe having the SEQ ID NO: 1 or a fragment thereof (including that of SEQ ID NO: 3), and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1× SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci staphylococci E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosoma episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HFGAN72X polypeptide is to be expressed for use in screening assays, generally, it is preferred that the polypeptide be produced at the surface of the cell. In this event, the cells may be harvested prior to use in the screening assay. If HFGAN72X polypeptide is secreted into the medium, the medium can be recovered in order to recover and purify the polypeptide; if produced intracellularly, the cells must first be lysed before the polypeptide is recovered.

HFGAN72X polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HFGAN72X polynucleotides for use as diagnostic reagents. Detection of a mutated form of the HFGAN72X gene associated with a dysfunction will provide a diagnostic tool that can add to or define a diagnosis of a disease or susceptibility to a disease which results from under-expression, over-expression or altered expression of HFGAN72X. Individuals carrying mutations in the HFGAN72X gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HFGAN72X nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985)230:1242. Sequence changes at specific locations may also be revealed by nuclease protection assays, such as RNase and S1 protection or the chemical cleavage method. See Cotton et al., *Proc Natl Acad Sci USA* (1985) 85:4397–4401. In another embodiment, an array of oligonucleotides probes comprising HFGAN72X nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the HFGAN72X gene by the methods described.

In addition, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of HFGAN72X polypeptide or HFGAN72X mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HFGAN72X, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof or cells expressing them can also be used as immunogens to produce antibodies immunospecific for the HFGAN72X polypeptides. The term "immunospecific"

means that the antibodies have substantially greater affinity for the polypeptides of the invention than their affinity for other related polypeptides in the prior art.

Antibodies generated against the HFGAN72X polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HFGAN72X polypeptides may also be employed to treat infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with HFGAN72X polypeptide, or a fragment thereof, adequate to produce antibody and/or T cell immune response to protect said animal from infections such as bacterial fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises, delivering HFGAN72X polypeptide via a vector directing expression of HFGAN72X polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HFGAN72X polypeptide wherein the composition comprises a HFGAN72X polypeptide or HFGAN72X gene. The vaccine formulation may further comprise a suitable carrier. Since HFGAN72X polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HFGAN72X polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991).

HFGAN72X polypeptides are responsible for many biological functions, including many pathologies. Accordingly, it is desirous to find compounds and drugs which stimulate HFGAN72X on the one hand and which can inhibit the function of HFGAN72X on the other hand. In general, agonists are employed for therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

In general, such screening procedures involve producing appropriate cells which express the receptor polypeptide of the present invention on the surface thereof. Such cells include cells from mammals, yeast, Drosophila or *E. coli*.

Cells expressing the receptor (or cell membrane containing the expressed receptor) are then contacted with a test compound to observe binding, or stimulation or inhibition of a functional response.

One screening technique includes the use of cells which express receptor of this invention (for example, transfected CHO cells) in a system which measures extracellular pH or intracellular calcium changes caused by receptor activation. In this technique, compounds may be contacted with cells expressing the receptor polypeptide of the present invention. A second messenger response, e.g., signal transduction, pH changes, or changes in calcium level, is then measured to determine whether the potential compound activates or inhibits the receptor.

Another method involves screening for receptor inhibitors by determining inhibition or stimulation of receptor-mediated cAMP and/or adenylate cyclase accumulation. Such a method involves transfecting a eukaryotic cell with the receptor of this invention to express the receptor on the cell surface. The cell is then exposed to potential antagonists in the presence of the receptor of this invention. The amount of cAMP accumulation is then measured. If the potential antagonist binds the receptor, and thus inhibits receptor binding, the levels of receptor-mediated cAMP, or adenylate cyclase, activity will be reduced or increased.

Another method for detecting agonists or antagonists for the receptor of the present invention is the yeast based technology as described in U.S. Pat. No. 5,482,835.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed. Standard methods for conducting such screening assays are well understood in the art.

Examples of potential HFGAN72X antagonists include antibodies or, in some cases, oligonucleotides or proteins which are closely related to the ligand of the HFGAN72X e.g., a fragment of the ligand, or small molecules which bind to the receptor but do not elicit a response, so that the activity of the receptor is prevented.

Prophylactic and Therapeutic Methods

This invention provides methods of treating abnormal conditions such as, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, related to both an excess of and insufficient amounts of HFGAN72X activity.

If the activity of HFGAN72X is in excess, several approaches are available. One approach comprises administering to a subject an inhibitor compound (antagonist) as hereinabove described along with a pharmaceutically acceptable carrier in an amount effective to inhibit activation by blocking binding of ligands to the HFGAN72X, or by inhibiting a second signal, and thereby alleviating the abnormal condition. In another approach, soluble forms of HFGAN72X polypeptides still capable of binding the ligand in competition with endogenous HFGAN72X may be administered. Typical embodiments of such competitors comprise fragments of the HFGAN72X polypeptide.

In still another approach, expression of the gene encoding endogenous HFGAN72X can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988)241:456; Dervan et al., *Science* (1991)251:1360. These oligomers can be administered per se or the relevant oligomers can be expressed in vivo.

For treating abnormal conditions related to an under-expression of HFGAN72X and its activity, several approaches are also available. One approach comprises administering to a subject a therapeutically effective amount of a compound which activates HFGAN72X i.e., an agonist as described above, in combination with a pharmaceutically acceptable carrier, to thereby alleviate the abnormal condition. Alternatively, gene therapy may be employed to effect the endogenous production of HFGAN72X by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996). Another approach is to administer a therapeutic amount of HFGAN72X polypeptides in combination with a suitable pharmaceutical carrier.

Formulation and Administration

Peptides, such as the soluble form of HFGAN72X polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

A human placenta genomic phage library was screened using standard hybridization techniques and using the cDNA clone (SEQ ID NO:3) as a probe. A subclone comprising the terminal region of the polypeptide was cloned using Sac I restriction endonuclease with standard techniques. As a results the HFGAN72X gene (SEQ ID NO: 1) was identified.

Example 2
Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

Example 3
Ligand Bank for Binding and Functional Assays

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

Example 4
Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal-to-noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 5
Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in $Ca^{2+}$ free Barth's medium at room temperature. The Xenopus system can be used to screen known ligands and tissue/cell extracts for activating ligands.

Example 6
Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer Molecular Devices Ltd., Menlo Park Calif.). The CYTOSENSOR is thus capable of detecting the activation of a receptor which is coupled to an energy utilizing intracellular signaling pathway such as the G-protein coupled receptor of the present invention.

Example 7
Extract/Cell Supernatant Screening

A large number of mammalian receptors exist for which there remains, as yet, no cognate activating ligand (agonist).

Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is isolated identified.

Example 8

Calcium and cAMP Functional Assays

7TM receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation ate tested in vector control cells to determine if the response is unique to the transfected cells expressing receptor

What is claimed is:

1. An isolated polynucleotide comprising a polynucleotide sequence encoding the polypeptide sequence as set forth in SEQ ID NO:2.

2. The polynucleotide of claim 1, wherein said polynucleotide is DNA.

3. The polynucleotide of claim 1, wherein said polynucleotide is RNA.

4. An isolated polynucleotide comprising the polynucleotide sequence as set forth in SEQ ID NO: 1.

5. The polynucleotide of claim 4, wherein said polynucleotide consists of the polynucleotide sequence as set forth in SEQ ID NO: 1.

6. An expression vector comprising a nucleic acid encoding a HFGAN72X polypeptide comprising the amino acid sequence as set forth in SEQ ID NO:2 when said expression vector is present in a compatible host cell.

7. An isolated host cell transfected or transformed with the expression vector of claim 6.

8. A process for producing a HFGAN72X polypeptide comprising culturing a host cell of claim 7 under conditions sufficient for the production of said polypeptide and recovering the polypeptide from the culture.

9. A process for producing a cell that produces a HFGAN72X polypeptide thereof comprising transforming or transfecting a host cell with the expression vector of claim 6 such that the host cell, under appropriate culture conditions, produces a HFGAN72X polypeptide.

10. A cell produced by the process of claim 9.

11. An isolated membrane of a cell of claim 10 expressing a polypeptide comprising the amino acid sequence as set forth in SEQ ID NO:2.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1564 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CCTCCCTTCA GGAAGTTTGA GGCTGAGACC CGAAAAGACC TGGGTGCAAG CCTCCAGGCA         60

CCCTGAAGGG AGTGGACTGA GGGCTGGCCC AAGCTCCCTC CTCTCCCTCT GTAGAGACTA        120

GGATGCCCCT CTGCTGCAGC GGCTCCTGAG CTCATGGAGC CCTCAGCCAC CCCAGGGGCC        180

CAGATGGGGG TCCCCCCTGG CAGCAGAGAG CCGTCCCCTG TGCCTCCAGA CTATGAAGAT        240

GAGTTTCTCC GCTATCTGTG GCGTGATTAT CTGTACCCAA AACAGTATGA GTGGGTCCTC        300

ATCGCAGCCT ATGTGGCTGT GTTCGTCGTG GCCCTGGTGG CAACACGCT GGTCTGCCTG         360

GCCGTGTGGC GGAACCACCA CATGAGGACA GTCACCAACT ACTTCATTGT CAACCTGTCC        420

CTGGCTGACG TTCTGGTGAC TGCTATCTGC CTGCCGGCCA GCCTGCTGGT GGACATCACT        480

GAGTCCTGGC TGTTCGGCCA TGCCCTCTGC AAGGTCATCC CCTATCTACA GGCTGTGTCC        540

GTGTCAGTGG CAGTGCTAAC TCTCAGCTTC ATCGCCCTGG ACCGCTGGTA TGCCATCTGC        600

CACCCACTAT TGTTCAAGAG CACAGCCCGG CGGGCCCGTG GCTCCATCCT GGGCATCTGG        660

GCTGTGTCGC TGGCCATCAT GGTGCCCCAG GCTGCAGTCA TGGAATGCAG CAGTGTGCTG        720

CCTGAGCTAG CCAACCGCAC ACGGCTCTTC TCAGTCTGTG ATGAACGCTG GGCAGATGAC        780

CTCTATCCCA AGATCTACCA CAGTTGCTTC TTTATTGTCA CCTACCTGGC CCCACTGGGC        840

CTCATGGCCA TGGCCTATTT CCAGATATTC CGCAAGCTCT GGGGCCGCCA GATCCCCGGC        900

ACCACCTCAG CACTGGTGCG GAACTGGAAG CGCCCCTCAG ACCAGCTGGG GGACCTGGAG        960

CAGGGCCTGA GTGGAGAGCC CCAGCCCCGG GGCCGCGCCT TCCTGGCTGA AGTGAAGCAG       1020

ATGCGTGCAC GGAGGAAGAC AGCCAAGATG CTGATGGTGG TGCTGCTGGT CTTCGCCCTC       1080

TGCTACCTGC CCATCAGCGT CCTCAATGTC CTTAAGAGGG TGTTCGGGAT GTTCCGCCAA       1140

GCCAGTGACC GCGAAGCTGT CTACGCCTGC TTCACCTTCT CCCACTGGCT GGTGTACGCC       1200

AACAGCGCTG CCAACCCCAT CATCTACAAC TTCCTCAGTG GCAAATTCCG GGAGCAGTTT       1260
```

-continued

```
AAGGCTGCCT TCTCCTGCTG CCTGCCTGGC CTGGGTCCCT GCGGCTCTCT GAAGGCCCCT    1320

AGTCCCCGCT CCTCTGCCAG CCACAAGTCC TTGTCCTTGC AGAGCCGATG CTCCATCTCC    1380

AAAATCTCTG AGCATGTGGT GCTCACCAGC GTCACCACAG TGCTGCCCTG AGCGAGGGCT    1440

GCCCTGGAGG CTCCGGCTCG GGGGATCTGC CCCTACCCCT CATGGAAAGA CAGCTGGATG    1500

TGGTGAAAGG CTGTGGATTC AGTCCTGGGT TTCTGCCTGT GTGACTCTGG ATAAGTCACT    1560

TCCT                                                                 1564
```

(2) INFORMATION FOR SEQ ID NO:2:

(i) SEQUENCE CHARACTERISTICS:
        (A) LENGTH: 425 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Pro Ser Ala Thr Pro Gly Ala Gln Met Gly Val Pro Pro Gly
 1               5                  10                  15

Ser Arg Glu Pro Ser Pro Val Pro Pro Asp Tyr Glu Asp Glu Phe Leu
         20                  25                  30

Arg Tyr Leu Trp Arg Asp Tyr Leu Tyr Pro Lys Gln Tyr Glu Trp Val
 35                  40                  45

Leu Ile Ala Ala Tyr Val Ala Val Phe Val Val Ala Leu Val Gly Asn
     50                  55                  60

Thr Leu Val Cys Leu Ala Val Trp Arg Asn His His Met Arg Thr Val
 65                  70                  75                  80

Thr Asn Tyr Phe Ile Val Asn Leu Ser Leu Ala Asp Val Leu Val Thr
             85                  90                  95

Ala Ile Cys Leu Pro Ala Ser Leu Leu Val Asp Ile Thr Glu Ser Trp
        100                 105                 110

Leu Phe Gly His Ala Leu Cys Lys Val Ile Pro Tyr Leu Gln Ala Val
115                 120                 125

Ser Val Ser Val Ala Val Leu Thr Leu Ser Phe Ile Ala Leu Asp Arg
        130                 135                 140

Trp Tyr Ala Ile Cys His Pro Leu Leu Phe Lys Ser Thr Ala Arg Arg
145                 150                 155                 160

Ala Arg Gly Ser Ile Leu Gly Ile Trp Ala Val Ser Leu Ala Ile Met
            165                 170                 175

Val Pro Gln Ala Ala Val Met Glu Cys Ser Ser Val Leu Pro Glu Leu
        180                 185                 190

Ala Asn Arg Thr Arg Leu Phe Ser Val Cys Asp Glu Arg Trp Ala Asp
195                 200                 205

Asp Leu Tyr Pro Lys Ile Tyr His Ser Cys Phe Phe Ile Val Thr Tyr
        210                 215                 220

Leu Ala Pro Leu Gly Leu Met Ala Met Ala Tyr Phe Gln Ile Phe Arg
225                 230                 235                 240

Lys Leu Trp Gly Arg Gln Ile Pro Gly Thr Thr Ser Ala Leu Val Arg
            245                 250                 255

Asn Trp Lys Arg Pro Ser Asp Gln Leu Gly Asp Leu Glu Gln Gly Leu
        260                 265                 270

Ser Gly Glu Pro Gln Pro Arg Gly Arg Ala Phe Leu Ala Glu Val Lys
275                 280                 285
```

```
Gln Met Arg Ala Arg Arg Lys Thr Ala Lys Met Leu Met Val Val Leu
    290                 295                 300

Leu Val Phe Ala Leu Cys Tyr Leu Pro Ile Ser Val Leu Asn Val Leu
305                 310                 315                 320

Lys Arg Val Phe Gly Met Phe Arg Gln Ala Ser Asp Arg Glu Ala Val
    325                 330                 335

Tyr Ala Cys Phe Thr Phe Ser His Trp Leu Val Tyr Ala Asn Ser Ala
    340                 345                 350

Ala Asn Pro Ile Ile Tyr Asn Phe Leu Ser Gly Lys Phe Arg Glu Gln
355                 360                 365

Phe Lys Ala Ala Phe Ser Cys Cys Leu Pro Gly Leu Gly Pro Cys Gly
    370                 375                 380

Ser Leu Lys Ala Pro Ser Pro Arg Ser Ser Ala Ser His Lys Ser Leu
385                 390                 395                 400

Ser Leu Gln Ser Arg Cys Ser Ile Ser Lys Ile Ser Glu His Val Val
    405                 410                 415

Leu Thr Ser Val Thr Thr Val Leu Pro
    420                 425

(2) INFORMATION FOR SEQ ID NO:3:

(i) SEQUENCE CHARACTERISTICS:
        (A) LENGTH: 1564 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CCTCCCTTCA GGAAGTTTGA GGCTGAGACC CGAAAAGACC TGGGTGCAAG CCTCCAGGCA      60

CCCTGAAGGG AGTGGACTGA GGGCTGGCCC AAGCTCCCTC CTCTCCCTCT GTAGAGACTA     120

GGATGCCCCT CTGCTGCAGC GGCTCCTGAG CTCATGGAGC CCTCAGCCAC CCCAGGGGCC     180

CAGATGGGGG TCCCCCCTGG CAGCAGAGAG CCGTCCCCTG TGCCTCCAGA CTATGAAGAT     240

GAGTTTCTCC GCTATCTGTG GCGTGATTAT CTGTACCCAA AACAGTATGA GTGGGTCCTC     300

ATCGCAGCCT ATGTGGCTGT GTTCGTCGTG GCCCTGGTGG CAACACGCT GGTCTGCCTG      360

GCCGTGTGGC GGAACCACCA CATGAGGACA GTCACCAACT ACTTCATTGT CAACCTGTCC     420

CTGGCTGACG TTCTGGTGAC TGCTATCTGC CTGCCGGCCA GCCTGCTGGT GGACATCACT     480

GAGTCCTGGC TGTTCGGCCA TGCCCTCTGC AAGGTCATCC CCTATCTACA GGCTGTGTCC     540

GTGTCAGTGG CAGTGCTAAC TCTCAGCTTC ATCGCCCTGG ACCGCTGGTA TGCCATCTGC     600

CACCCACTAT TGTTCAAGAG CACAGCCCGG CGGGCCCGTG GCTCCATCCT GGGCATCTGG     660

GCTGTGTCGC TGGCCATCAT GGTGCCCCAG GCTGCAGTCA TGGAATGCAG CAGTGTGCTG     720

CCTGAGCTAG CCAACCGCAC ACGGCTCTTC TCAGTCTGTG ATGAACGCTG GCAGATGAC      780

CTCTATCCCA AGATCTACCA CAGTTGCTTC TTTATTGTCA CCTACCTGGC CCCACTGGGC     840

CTCATGGCCA TGGCCTATTT CCAGATATTC CGCAAGCTCT GGGGCCGCCA GATCCCCGGC     900

ACCACCTCAG CACTGGTGCG GAACTGGAAG CGCCCCTCAG ACCAGCTGGG GGACCTGGAG     960

CAGGGCCTGA GTGGAGAGCC CCAGCCCCGG GGCCGCGCCT TCCTGGCTGA AGTGAAGCAG    1020

ATGCGTGCAC GGAGGAAGAC AGCCAAGATG CTGATGGTGG TGCTGCTGGT CTTCGCCCTC    1080

TGCTACCTGC CCATCAGCGT CCTCAATGTC CTTAAGAGGG TGTTCGGGAT GTTCCGCCAA    1140

GCCAGTGACC GCGAAGCTGT CTACGCCTGC TTCACCTTCT CCCACTGGCT GGTGTACGCC    1200
```

```
AACAGCGCTG CCAACCCCAT CATCTACAAC TTCCTCAGTG GCAAATTCCG GGAGCAGTTT    1260

AAGGCTGCCT TCTCCTGCTG CCTGCCTGGC CTGGGTCCCT GCGGCTCTCT GAAGGCCCCT    1320

AGTCCCCGCT CCTCTGCCAG CCACAAGTCC TTGTCCTTGT AGAGCCGATG CTCCGTCTCC    1380

AAAATCTCTG AGCATGTGGT GCTCACCAGC GTCACCACAG TGCTGCCCTG AGCGAGGGCT    1440

GCCCTGGAGG CTCCGGNTCG GGGGATCTGC CCCTACCCCT CATGGNAAGA CAGCTGGATG    1500

TGGTGAAAGG CTGTGGATTC AGNCCTGGGT TTCTGCCTGT GTGACTCTGG ATAAGTCANT    1560

TCCT                                                                1564
```

(2) INFORMATION FOR SEQ ID NO:4:

(i) SEQUENCE CHARACTERISTICS:
        (A) LENGTH: 402 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Glu Pro Ser Ala Thr Pro Gly Ala Gln Met Gly Val Pro Pro Gly
 1               5                  10                  15

Ser Arg Glu Pro Ser Pro Val Pro Pro Asp Tyr Glu Asp Glu Phe Leu
            20                  25                  30

Arg Tyr Leu Trp Arg Asp Tyr Leu Tyr Pro Lys Gln Tyr Glu Trp Val
    35                  40                  45

Leu Ile Ala Ala Tyr Val Ala Val Phe Val Val Ala Leu Val Gly Asn
50                  55                  60

Thr Leu Val Cys Leu Ala Val Trp Arg Asn His His Met Arg Thr Val
65                  70                  75                  80

Thr Asn Tyr Phe Ile Val Asn Leu Ser Leu Ala Asp Val Leu Val Thr
85                  90                  95

Ala Ile Cys Leu Pro Ala Ser Leu Leu Val Asp Ile Thr Glu Ser Trp
            100                 105                 110

Leu Phe Gly His Ala Leu Cys Lys Val Ile Pro Tyr Leu Gln Ala Val
115                 120                 125

Ser Val Ser Val Ala Val Leu Thr Leu Ser Phe Ile Ala Leu Asp Arg
            130                 135                 140

Trp Tyr Ala Ile Cys His Pro Leu Leu Phe Lys Ser Thr Ala Arg Arg
145                 150                 155                 160

Ala Arg Gly Ser Ile Leu Gly Ile Trp Ala Val Ser Leu Ala Ile Met
            165                 170                 175

Val Pro Gln Ala Ala Val Met Glu Cys Ser Ser Val Leu Pro Glu Leu
            180                 185                 190

Ala Asn Arg Thr Arg Leu Phe Ser Val Cys Asp Glu Arg Trp Ala Asp
195                 200                 205

Asp Leu Tyr Pro Lys Ile Tyr His Ser Cys Phe Phe Ile Val Thr Tyr
            210                 215                 220

Leu Ala Pro Leu Gly Leu Met Ala Met Ala Tyr Phe Gln Ile Phe Arg
225                 230                 235                 240

Lys Leu Trp Gly Arg Gln Ile Pro Gly Thr Thr Ser Ala Leu Val Arg
            245                 250                 255

Asn Trp Lys Arg Pro Ser Asp Gln Leu Gly Asp Leu Glu Gln Gly Leu
            260                 265                 270
```

-continued

```
Ser Gly Glu Pro Gln Pro Arg Ala Arg Ala Phe Leu Ala Glu Val Lys
275                 280                 285

Gln Met Arg Ala Arg Lys Thr Ala Lys Met Leu Met Val Val Leu
    290                 295                 300

Leu Val Phe Ala Leu Cys Tyr Leu Pro Ile Ser Val Leu Asn Val Leu
305                 310                 315                 320

Lys Arg Val Phe Gly Met Phe Arg Gln Ala Ser Asp Arg Glu Ala Val
325                 330                 335

Tyr Ala Cys Phe Thr Phe Ser His Trp Leu Val Tyr Ala Asn Ser Ala
    340                 345                 350

Ala Asn Pro Ile Ile Tyr Asn Phe Leu Ser Gly Lys Phe Arg Glu Gln
355                 360                 365

Phe Lys Ala Ala Phe Ser Cys Cys Leu Pro Gly Leu Gly Pro Cys Gly
    370                 375                 380

Ser Leu Lys Ala Pro Ser Pro Arg Ser Ser Ala Ser His Lys Ser Leu
385                 390                 395                 400

Ser Leu
```